US007918903B2

(12) United States Patent
Audousset et al.

(10) Patent No.: US 7,918,903 B2
(45) Date of Patent: Apr. 5, 2011

(54) COMPOSITION FOR THE OXIDATION DYEING OF KERATIN FIBERS COMPRISING AT LEAST ONE FATTY SUBSTANCE AND AT LEAST ONE N,N BIS(BETA-HYDROXYETHYL)-PARA-PHENYLENEDIAMINE

(75) Inventors: Marie-Pascale Audousset, Asnieres (FR); Isabelle Schlosser, Paris (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 12/642,543

(22) Filed: Dec. 18, 2009

(65) Prior Publication Data
US 2010/0154142 A1 Jun. 24, 2010

Related U.S. Application Data

(60) Provisional application No. 61/150,915, filed on Feb. 9, 2009.

(30) Foreign Application Priority Data

Dec. 19, 2008 (FR) .................................. 08 07319

(51) Int. Cl.
*A61Q 5/10* (2006.01)
(52) U.S. Cl. .............. 8/405; 8/406; 8/410; 8/411; 8/421; 8/435; 8/604; 8/620
(58) Field of Classification Search .............. 8/405, 406, 8/410, 411, 421, 435, 604, 620
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,845,293 A * | 7/1989 | Junino et al. | 564/441 |
| 5,021,066 A | 6/1991 | Aeby et al. | |
| 5,259,849 A | 11/1993 | Grollier et al. | |
| 5,364,414 A | 11/1994 | Lang et al. | |
| 5,817,155 A | 10/1998 | Yasuda et al. | |
| 6,010,541 A | 1/2000 | De La Mettrie | |
| 6,074,439 A | 6/2000 | De La Mettrie et al. | |
| 6,129,770 A | 10/2000 | Deutz et al. | |
| 6,156,713 A | 12/2000 | Colgate-Palmolive | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 | 11/2003 | Vidal et al. | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,799,095 B2 | 9/2010 | Mario et al. | |

(Continued)

FOREIGN PATENT DOCUMENTS

CA 1 268 421 5/1990

(Continued)

OTHER PUBLICATIONS

French Search Report for FR 0807319, dated Aug. 3, 2009.
English language abstract of DE 10 2006 012 575 A1, Feb. 8, 2007.
English language abstract of FR 2 779 949 A1, Dec. 24, 1999.
English language abstract of JP 2003-238370, Aug. 27, 2003.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.

(Continued)

Primary Examiner — Eisa B Elhilo
(74) Attorney, Agent, or Firm — Finnegan, Henderson, Farabow, Garrett & Dunner, LLP

(57) ABSTRACT

The present disclosure relates to a composition for the oxidation dyeing of keratin fibers, for example human keratin fibers such as the hair, comprising: at least one fatty substance present in an amount greater than or equal to 20% by weight relative to the total weight of the composition; at least one oxidation base chosen from N,N-(β-hydroxyethyl)-para-phenylenediamines and the addition salts thereof with an acid, at least one dye precursor different than the at least one oxidation base chosen from N,N-(β-hydroxyethyl)-para-phenylenediamines and the addition salts thereof with an acid, at least one oxidizing agent, and optionally at least one alkaline agent. The disclosure also relates to a dyeing or lightening process using it. Another aspect of the disclosure is multi-compartment devices or kits for obtaining, after mixing together the compositions of the compartments, just before its application, a composition according to the disclosure.

18 Claims, No Drawings

U.S. PATENT DOCUMENTS

| | | |
|---|---|---|
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | DeCoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 A1 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 A1 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 A1 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |

| WO | WO 2008/096497 | 8/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Jan. 2, 1992.
English language Abstract of DE 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Octoer 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.

Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Sep. 7, 2010, in U.S. Appl. No. 12/642,599.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

COMPOSITION FOR THE OXIDATION DYEING OF KERATIN FIBERS COMPRISING AT LEAST ONE FATTY SUBSTANCE AND AT LEAST ONE N,N BIS(BETA-HYDROXYETHYL)-PARA-PHENYLENEDIAMINE

This application claims benefit of U.S. Provisional Application No. 61/150,915, filed Feb. 9, 2009. This application also claims benefit of priority under 35 U.S.C. §119 to French Patent Application No. 0807319, filed Dec. 19, 2008.

The present disclosure relates to a composition for the oxidation dyeing of keratin fibers.

It is known practice to dye keratin fibers, such as human hair, with dye compositions containing oxidation dyes, for example oxidation dye precursors and coloring modifiers.

Oxidation dye precursors, generally known as oxidation bases, are initially colorless or weakly colored compounds which, in combination with oxidizing products, can give rise, via an oxidative condensation process, to colored and coloring compounds. They include, for example, compounds such as ortho- or para-phenylenediamines, ortho- or para-aminophenols and heterocyclic bases.

It is also known that it is possible to vary the shades obtained with these oxidation bases by combining them with couplers or coloring modifiers, the latter generally being chosen from meta-diaminobenzenes, meta-aminophenols, meta-diphenols and certain heterocyclic compounds such as indole compounds.

The variety of the molecules involved as oxidation bases and couplers can make it possible to obtain a rich range of colors.

It is desired that the "permanent" coloring obtained by virtue of these oxidation dyes, also called oxidation dyeing, should, moreover, meet at least one of a certain number of requirements. Thus, it should have no toxicological drawbacks, it should allow shades to be obtained in the desired strength, and it should show good fastness with respect to external attacks such as light, bad weather, washing, permanent-waving, perspiration and rubbing.

The dyes should also allow white hair to be covered and, finally, should be as nonselective as possible, i.e. they should make it possible to obtain the smallest possible differences in coloring right the way along the same keratin fiber, which is generally differently sensitized (i.e. damaged) between its tip and its root.

Many attempts have been made, in the hair-dyeing field, to improve the dyeing properties via, for example, adjuvants. However, the choice of these adjuvants is tricky insofar as they should improve the dyeing properties of the dye compositions without being detrimental to the other properties of these compositions. For example, these adjuvants should not be detrimental to the keratin fiber-lightening properties and the coloring application properties.

Accordingly, one aspect of the present disclosure is novel compositions for the oxidation dyeing of keratin fibers which do not have at least one of the drawbacks of the prior art. For example, another aspect of the present disclosure is compositions for the oxidation dyeing of keratin fibers, which may have improved dyeing properties and which can be easy to mix and to apply, for instance which do not run and which may remain localized at the point of application. The term "improved dyeing properties" is intended to mean an improvement in the level of strength/intensity and/or homogeneity of the dyeing.

Thus, at least one of these aims may be achieved by virtue of the present disclosure, one aspect of which is a composition for the oxidation dyeing of keratin fibers, for example human keratin fibers such as the hair, comprising:
  at least one fatty substance present in an amount greater than or equal to 25% by weight relative to the total weight of the composition,
  at least one oxidation base chosen from N,N-(β-hydroxyethyl)-para-phenylenediamines and the addition salts thereof with an acid,
  at least one dye precursor different than the at least on oxidation base,
  at least one oxidizing agent, and
  optionally at least one alkaline agent.

The composition according to the present disclosure may have improved dyeing properties. For example, the composition of the disclosure may result in colorings which exhibit good strength and/or intensity and/or good homogeneity of the color along the fiber between the end and the root of the hairs (also referred to as coloring selectivity) and/or good chromaticity. The composition of the disclosure may be applied to keratin fibers without difficulty, and without running. This composition also may make it possible to obtain reduced degradation of the keratin fibers during the dyeing process.

For example, the colorings obtained via the compositions of the disclosure may be fast, and withstand the various external attacks that keratin fibers may be subjected to.

One aspect of the present disclosure is also a process for dyeing keratin fibers using the composition in accordance with the disclosure.

Another aspect of the present disclosure is also a multi-compartment device for using the composition of the disclosure.

Another aspect of the present disclosure is the use of the composition in accordance with the disclosure, for the oxidation dyeing of keratin fibers.

As has been mentioned, the composition of the disclosure comprises at least one fatty substance.

The term "fatty substance" is intended to mean an organic compound which is insoluble in water at normal temperature (25° C.) and at atmospheric pressure (760 mmHg) (solubility of less than 5%, such as less than 1%, or such as less than 0.1%). They have, in their structure, a sequence of at least two siloxane groups or at least one hydrocarbon-based chain containing at least six carbon atoms. In addition, fatty substances are generally soluble in organic solvents under the same temperature and pressure conditions, for instance chloroform, ethanol, benzene or decamethylcyclopentasiloxane.

In at least one embodiment, the at least one fatty substance is different from fatty acid.

In some embodiments, the at least one fatty substance is chosen from lower alkanes, fatty alcohols, fatty acid esters, fatty alcohol esters, oils, such as nonsilicone mineral, plant, animal and synthetic oils, nonsilicone waxes and silicones.

For the purpose of the disclosure, the fatty alcohols, fatty esters and fatty acid esters contain at least one saturated or unsaturated, linear or branched hydrocarbon-based group containing from 6 to 30 carbon atoms, which is optionally substituted, for example with at least one hydroxyl group (for example from 1 to 4). If they are unsaturated, these compounds may comprise one to three conjugated or nonconjugated carbon-carbon double bonds.

With regard to the lower alkanes, they may, for example, contain from 6 to 16 carbon atoms and are linear or branched, and optionally cyclic. By way of example, the alkanes may be chosen from hexane, dodecane, and isoparaffins such as isohexadecane and isodecane.

As nonsilicone oils that can be used in the composition of the disclosure, mention may, for example, be made of:

hydrocarbon-based oils of animal origin, such as perhydrosqualene;

hydrocarbon-based oils of plant origin, such as liquid triglycerides of fatty acids containing from 6 to 30 carbon atoms, for instance triglycerides of heptanoic acid or octanoic acid or alternatively, for example, sunflower oil, corn oil, soya oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names MIGLYOL® 810, 812 and 818 by the company Dynamit Nobel, jojoba oil, shea butter oil;

linear or branched hydrocarbons containing more than 16 carbon atoms, of mineral or synthetic origin, such as volatile or nonvolatile liquid paraffins, and derivatives thereof, petroleum jelly, liquid petroleum jelly, polydecenes, hydrogenated polyisobutene such as PARLEAM®;

partially hydrocarbon-based fluoro oils; as fluoro oils, exemplary mention may also be made of perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else the bromoperfluorooctyl sold under the name FORALKYL® by the company Atochem; nonafluoromethoxybutane and nonafluoroethoxyisobutane; perfluoromorpholine derivatives, such as 4-trifluoromethyl perfluoromorpholine sold under the name PF 5052® by the company 3M.

The fatty alcohols that can be used as fatty substances in the composition of the disclosure are nonoxyalkylenated, saturated or unsaturated, linear or branched, and contain 6 to 30 carbon atoms, for example from 8 to 30 carbon atoms; exemplary mention may be made of cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The nonsilicone wax(es) that can be used in the composition of the disclosure is (are) chosen, for example, from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that can be used according to the disclosure include, for example, marine waxes such as the product sold by the company Sophim under the reference M82, and polyethylene waxes or polyolefin waxes in general.

In at least one embodiment, the esters are chosen from esters of saturated or unsaturated, linear or branched C1-C26 aliphatic mono- or polyacids and of saturated or unsaturated, linear or branched C1-C26 aliphatic mono- or polyalcohols, the total carbon number of the esters, for example, being greater than or equal to 10.

Among the monoesters, exemplary mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyle erucate; oleyl erucate; ethyl and isopropyl palmitates, 2-ethylhexyl palmitate, 2-octyldecyl palmitate, alkyl myristates such as isopropyl myristate, butyl myristate, cetyl myristate, 2-octyldodecyl myristate, mirystyl myristate or stearyl myristate, hexyl stearate, butyl stearate, isobutyl stearate; dioctyl malate, hexyl laurate, and 2-hexyldecyl laurate.

In at least one embodiment, these esters are chosen from esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

Exemplary mention may also be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisonoanonate; and polyethylene glycol distearates.

Among the esters mentioned above, in at least one embodiment, the ester is chosen from ethyl palmitate, isopropyl palmitate, myristyl palmitate, cetyl palmitate, stearyl palmitate, 2-ethylhexyl palmitate, 2-octyldecyl palmitate, alkyl myristates such as isopropyl myristate, butyl myristate, cetyl myristate and 2-octyldodecyl myristate, hexyl stearate, butyl stearate, isobutyl stearate; dioctyl malate, hexyl laurate, 2-hexyldecyl laurate, isononyl isononanate and cetyl octanoate.

In some embodiments, the composition may also comprise, as fatty ester, sugar esters and diesters of $C_6$-$C_{30}$, and in at least one embodiment $C_{12}$-$C_{22}$, fatty acids. As used herein, the term "sugar" is intended to mean oxygen-bearing hydrocarbon-based compounds containing several alcohol functions, with or without aldehyde or ketone functions, and which contain at least four carbon atoms. These sugars may be monosaccharides, oligosaccharides or polysaccharides.

As suitable sugars, mention may, for example, be made of sucrose (or saccharose), glucose, galactose, ribose, fucose, maltose, fructose, mannose, arabinose, xylose and lactose, and derivatives thereof, for example alkyl derivatives, such as methyl derivatives, for instance methylglucose.

In at least one embodiment, the sugar esters of fatty acids may be chosen from the group comprising the esters or mixtures of esters of sugars described previously, linear or branched, saturated or unsaturated $C_6$-$C_{30}$ fatty acid esters, such as $C_{12}$-$C_{22}$, fatty acid esters, and mixtures thereof. If they are unsaturated, these compounds may comprise one to three conjugated or nonconjugated carbon-carbon double bonds.

The esters according to this embodiment may also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates, arachidonates, and mixtures thereof, such as oleo-palmitate, oleo-stearate and palmito-stearate mixed esters.

In at least one embodiment, the esters are chosen from monoesters and diesters, for example from sucrose, glucose and methylglucose mono- or dioleates, stearates, behenates, oleopalmitates, linoleates, linolenates and oleostearates.

By way of example, mention may be made of the product sold under the name GLUCATE® DO by the company Amerchol, which is a methylglucose dioleate.

By way of examples of esters or mixtures of esters of sugar and of fatty acid, mention may also be made of the following:
the products sold under the names F160, F140, F110, F90, F70, SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name RYOTO SUGAR ESTERS, for example referenced B370 and corresponding to sucrose behenate formed from 20% monoester and 80% diester-triester-polyester;
the sucrose mono-dipalmito-stearate sold by the company Goldschmidt under the name TEGOSOFT® PSE.

The silicones that can be used in the composition of the present disclosure are volatile or nonvolatile, cyclic, linear or branched silicones which are unmodified or modified with organic groups, having a viscosity ranging from $5 \times 10^{-6}$ to 2.5 $m^2/s$ at 25° C., for example from $1 \times 10{-5}$ to 1 $m^2/s$.

The silicones that can be used in accordance with the disclosure may be in the form of oils, waxes, resins or gums.

In at least one embodiment, the silicone is chosen from polydialkylsiloxanes, and in at least one embodiment is chosen from polydimethyl-siloxanes (PDMS), and organomodified polysiloxanes comprising at least one functional group chosen from poly(oxyalkylene) groups, amino groups and alkoxy groups.

The organopolysiloxanes are defined in greater detail in Walter Noll's "Chemistry and Technology of Silicones" (1968), Academie Press. They can be volatile or nonvolatile.

When they are volatile, the silicones are, for example, chosen from those having a boiling point ranging from 60° C. to 260° C., and in some embodiments are chosen from:
(i) cyclic polydialkylsiloxanes containing from 3 to 7, such as from 4 to 5 silicon atoms. They are for example octamethylcyclotetrasiloxane sold, for example under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Exemplary mention may also be made of cyclocopolymers of the dimethylsiloxane/methylalkylsiloxane type, such as VOLATILE SILICONE® FZ 3109 sold by the company Union Carbide, of formula:

$$\boxed{\text{D''-D'} \underline{\qquad} \text{D''-D'}}$$

with D'': $-\underset{\underset{CH_3}{|}}{\overset{\overset{CH_3}{|}}{Si}}-O-$   with D': $-\underset{\underset{C_8H_{17}}{|}}{\overset{\overset{CH_3}{|}}{Si}}-O-$ Exemplary mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing from 2 to 9 silicon atoms and having a viscosity of less than or equal to $5 \times 10^{-6}$ $m^2/s$ at 25° C. An example is decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers "Volatile Silicone fluids for cosmetics".

In at least one embodiment, nonvolatile polydialkylsiloxanes, polydialkylsiloxane gums and resins, polyorganosiloxanes modified with organofunctional groups above, and mixtures thereof, are used.

These silicones are, in some embodiments, chosen from polydialkylsiloxanes, among which exemplary mention may be made of polydimethylsiloxanes containing trimethylsilyl end groups. The viscosity of the silicones is measured at 25° C. according to ASTM standard 445 Appendix C.

Among these polydialkylsiloxanes, exemplary mention may be made, in a nonlimiting manner, of the following commercial products:
the SILBIONE® oils of the 47 and 70 047 series or the MIRASIL® oils sold by Rhodia, for instance the oil 70 047 V 500 000;
the oils of the MIRASIL® series sold by the company Rhodia;
the oils of the 200 series from the company Dow Corning, such as DC200 with a viscosity of 60,000 $mm^2/s$;
the VISCASIL® oils from General Electric and certain oils of the SF series (SF 96, SF 18) from General Electric.

Exemplary mention may also be made of polydimethylsiloxanes containing dimethylsilanol end groups known under the name dimethiconol (CTFA), such as the oils of the 48 series from the company Rhodia.

In this category of polydialkylsiloxanes, exemplary mention may also be made of the products sold under the names ABIL WAX® 9800 and 9801 by the company Goldschmidt which are poly(C1-C20)dialkylsiloxanes.

The silicone gums that can be used in accordance with the disclosure are, for example, polydialkylsiloxanes, such as polydimethylsiloxanes with high number-average molecular masses ranging from 200,000 to 1,000,000, used alone or as a mixture in a solvent. This solvent may be chosen, for example, from volatile silicones, polydimethylsiloxane (PDMS) oils, polyphenylmethylsiloxane (PPMS) oils, isoparaffins, polyisobutylenes, methylene chloride, pentane, dodecane, tridecane, or mixtures thereof.

For example, products that can be used in accordance with the disclosure are mixtures chosen from:
mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
mixtures of a polydimethylsiloxane gum and of a cyclic silicone, such as the product SF 1214 SILICONE FLUID from the company General Electric; this product is an SF 30 gum corresponding to a dimethicone, having a number-average molecular weight of 500,000, dissolved in the oil SF 1202 Silicone Fluid corresponding to decamethylcyclopentasiloxane;
mixtures of two PDMSs with different viscosities, for instance of a PDMS gum and of a PDMS oil, such as the product SF 1236 from the company General Electric.

The product SF 1236 is a mixture of an SE 30 gum defined above, having a viscosity of 20 m²/s, and an SF 96 oil, having a viscosity of 5×10⁻⁶ m²/s. This product may, for example, contain 15% SE 30 gum and 85% SF 96 oil.

The organopolysiloxane resins that can be used in accordance with the disclosure are crosslinked siloxane systems containing the following units:

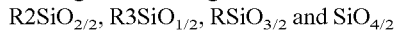

wherein R represents an alkyl containing 1 to 16 carbon atoms. In at least one embodiment, R denotes a $C_1$-$C_4$ lower alkyl group, and in at least one embodiment R is methyl.

Among these resins, exemplary mention may be made of the product sold under the name DOW CORNING 593 or those sold under the names SILICONE FLUID SS 4230 and SS 4267 by the company General Electric, and which are silicones of dimethyl/trimethyl siloxane structure.

Exemplary mention may also be made of the trimethylsiloxysilicate type resins sold, for example under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based group.

Besides the silicones described above, the organomodified silicones may be polydiarylsiloxanes, such as polydiphenylsiloxanes, and polyalkylaryl-siloxanes functionalized with the organofunctional groups mentioned previously.

The polyalkylarylsiloxanes are chosen, in some embodiments, from linear and/or branched polydimethyl/methyl phenylsiloxanes and polydimethyl/diphenylsiloxanes with a viscosity ranging from 1×10-5 to 5×10-2 m²/s at 25° C.

Among these polyalkylarylsiloxanes, mention may, by way of example, be made of the products sold under the following names:

the SILBIONE® oils of the 70 641 series from Rhodia;
the oils of the RHODORSIL® 70 633 and 763 series from Rhodia;
the oil DOW CORNING 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, exemplary mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 from the company Union Carbide, and the ($C_{12}$)alkylmethicone copolyol sold by the company Dow Corning under the name Q2 5200;
substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups;
alkoxylated groups such as the product sold under the name SILICONE COPOLYMER F-755 by SWS Silicones, and ABIL WAX® 2428, 2434 and 2440 by the company Goldschmidt.

In at least one embodiment, the at least one fatty substance is neither oxyalkylenated nor glycerolated.

In some embodiments, the at least one fatty substance is chosen from compounds that are liquid or pasty at ambient temperature and at atmospheric pressure.

In at least one embodiment, the at least one fatty substance is a compound that is liquid at a temperature of 25° C. and at atmospheric pressure.

In at least one embodiment, the at least one fatty substance is chosen from lower alkanes, fatty alcohols, fatty acid esters, fatty alcohol esters, oils, such as nonsilicone mineral, plant and synthetic oils, and silicones.

According to at least one embodiment, the at least one fatty substance is chosen from liquid petroleum jelly, polydecenes and liquid fatty acid esters, and liquid fatty alcohol esters; in at least one embodiment, the at least one fatty substance of the composition according to the disclosure is non-silicone-based.

In at least one embodiment, alkanes or hydrocarbons and silicones are chosen.

The composition according to the disclosure comprises at least one fatty substance present in an amount greater than or equal to 20% by weight relative to the total weight of the composition. In some embodiments, the at least one fatty substance is present in an amount ranging from 25% to 80%, or for example from 25% to 65%, or for example from 30% to 55% relative to the total weight of the composition.

In at least one embodiment, the at least one oxidation base chosen from N,N-bis(β-hydroxyethyl)-para-phenylenediamines and the addition salts thereof with an acid is present in the composition in a total amount ranging from 0.0005% to 12% by weight relative to the total weight of the composition, for example from 0.005% to 8% by weight, or for example from 0.05% to 5% by weight relative to the total weight of the composition.

In at least one embodiment, in addition to the at least one oxidation base chosen from N,N-bis(β-hydroxyethyl)-para-phenylenediamines and the addition salts thereof with an acid, the composition further comprises at least one dye precursor different than the at least one oxidation base.

In at least one embodiment, the at least one additional dye precursor different than the at least one oxidation base is chosen from oxidation bases other than N,N-bis(β-hydroxyethyl)-para-phenylenediamines and the addition salts thereof with an acid, and couplers.

For example, the at least one oxidation base other than N,N-bis(β-hydroxyethyl)-para-phenylenediamines and the addition salts thereof with an acid that can be used in the context of the present disclosure is chosen from those conventionally known in oxidation dyeing, and among which exemplary mention may be made of ortho- and para-phenylenediamines other than N,N-bis(β-hydroxyethyl)-para-phenylenediamine and the addition salts thereof with an acid, double bases, ortho- and para-aminophenols, heterocyclic bases, and the addition salts thereof with an acid.

In at least one embodiment, the at least one oxidation base other than N,N-bis(β-hydroxyethyl)-para-phenylenediamines and the addition salts thereof with an acid may be cationic.

The para-phenylenediamines that can be used in the context of the disclosure may, in at least one embodiment, be chosen from the compounds of formula (II) below and addition salts thereof with an acid:

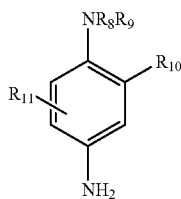

(II)

wherein:
- $R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous, phenyl or 4'-aminophenyl group;
- $R_9$ represents a hydrogen atom, a $C_1$-$C_4$ alkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous group;
- $R_8$ and $R_9$ may also form, with the nitrogen atom which bears them, a nitrogenous heterocycle containing 5 or 6 ring members, optionally substituted with at least one group chosen from alkyl, hydroxyl and ureido groups;
- $R_{10}$ represents a hydrogen atom, a halogen atom such as a chlorine atom, or a $C_1$-$C_4$ alkyl, sulfo, carboxyl, $C_1$-$C_4$ monohydroxyalkyl or $C_1$-$C_4$ hydroxyalkoxy, $C_1$-$C_4$ acetylaminoalkoxy, $C_1$-$C_4$ mesylaminoalkoxy or $C_1$-$C_4$ carbamoylaminoalkoxy radical;
- $R_{11}$ represents a hydrogen or halogen atom or a $C_1$-$C_4$ alkyl radical.

Among the nitrogenous groups in formula (II) above, exemplary mention may be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the para-phenylenediamines of formula (II) above, exemplary mention maybe made of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-((3-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and addition salts thereof with an acid.

In at least one embodiment, the para-phenylenediamines of formula (II) above are chosen from para-phenylenediamine, para-toluoylenediamine, 2-isopropyl-para-phenylenediamine, 2-β-hydroxyethyl-para-phenylenediamine, 2,6-dimethyl-para-phenylenediamine, 2,6-diethyl-para-phenylenediamine, 2,3-dimethyl-para-phenylenediamine, 2-chloro-para-phenylenediamine, and the addition salts thereof with an acid.

In at least one embodiment, the para-phenylenediamines of formula (II) above are chosen from para-phenylenediamine, para-toluoylenediamine, and the addition salts thereof with an acid.

According to the disclosure, the term "double bases" is intended to mean compounds comprising at least two aromatic rings on which amino and/or hydroxyl groups are carried.

In at least one embodiment, the at least one oxidation base other than N,N-bis(β-hydroxyethyl)-para-phenylenediamines and the addition salts thereof with an acid is a double base. Among the double bases that can be used in the composition in accordance with the disclosure, exemplary mention may be made of the compounds of formula (III) below and the addition salts thereof with an acid:

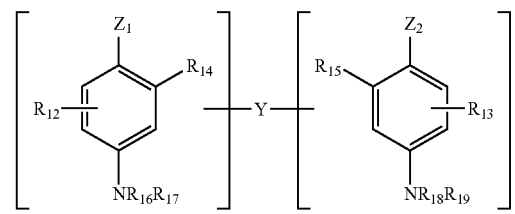

(III)

wherein:
- $Z_1$ and $Z_2$, which may be identical or different, represent a hydroxyl or —$NH_2$ radical that may be substituted with a $C_1$-$C_4$ alkyl radical or with a linker arm Y;
- the linker arm Y represents a linear or branched alkylene chain containing from 1 to 14 carbon atoms, that may be interrupted or terminated with at least one nitrogenous group and/or with at least one heteroatom such as oxygen, sulfur or nitrogen atoms, and optionally substituted with one or more hydroxyl or $C_1$-$C_6$ alkoxy radicals;
- $R_{12}$ and $R_{13}$ represent a hydrogen or halogen atom, a $C_1$-$C_4$ alkyl, $C_1$-$C_4$ monohydroxyalkyl, $C_2$-$C_4$ polyhydroxyalkyl or $C_1$-$C_4$ aminoalkyl radical, or a linker arm Y;
- $R_{14}$, $R_{15}$, $R_{16}$, $R_{17}$, $R_{18}$ and $R_{19}$, which may be identical or different, represent a hydrogen atom, a linker arm Y or a $C_1$-$C_4$ alkyl radical;
- it being understood that the compounds of formula (III) comprise only one linker arm Y per molecule.

Among the nitrogenous groups in formula (III) above, exemplary mention may be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the double bases of formulae (III) above, exemplary mention may be made of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and the addition salts thereof with an acid.

In at least one embodiment, the at least one base of formula (III) is chosen from N,N'-bis(β-hydroxyethyl)-N,N'-bis(4'- aminophenyl)-1,3-diaminopropanol, 1,8-bis(2,5-diaminophenoxy)-3,5-dioxaoctane, and the addition salts thereof with an acid.

For example, the para-aminophenols that can be used in the context of the disclosure may be chosen from the compounds of formula (IV) below and the addition salts thereof with an acid:

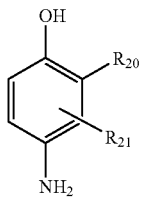

(IV)

wherein:
R$_{20}$ represents a hydrogen atom, a halogen atom such as fluorine, or a C$_1$-C$_4$ alkyl, C$_1$-C$_4$ monohydroxyalkyl, (C$_1$-C$_4$)alkoxy(C$_1$-C$_4$)alkyl, C$_1$-C$_4$ aminoalkyl or a (C$_1$-C$_4$)hydroxyalkyl(C$_1$-C$_4$)aminoalkyl radical;
R$_{21}$ represents a hydrogen atom or a halogen atom such as fluorine, or a C$_1$-C$_4$ alkyl, C$_1$-C$_4$ monohydroxyalkyl, C$_2$-C$_4$ polyhydroxyalkyl, C$_1$-C$_4$ aminoalkyl, C$_1$-C$_4$ cyanoalkyl or (C$_1$-C$_4$)alkoxy(C$_1$-C$_4$)alkyl radical.

Among the para-aminophenols of formula (IV) above, exemplary mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and the addition salts thereof with an acid.

In at least one embodiment, para-aminophenol and 4-amino-3-methylphenol are used.

The ortho-aminophenols that can be used in the context of the present disclosure are, for example, chosen from 2-aminophenol, 2-amino-1-hydroxy-5-methylbenzene, 2-amino-1-hydroxy-6-methylbenzene, 5-acetamido-2-aminophenol, and the addition salts thereof with an acid.

Among the heterocyclic bases that can be used in the composition in accordance with the disclosure, exemplary mention may be made of pyridine derivatives, pyrimidine derivatives and pyrazole derivatives, and the addition salts thereof with an acid.

Among the pyridine derivatives, exemplary mention may be made of the compounds described, for example, in patents GB 1 026 978 and GB 1 153 196, for instance 2,5-diaminopyridine, 2-(4-methoxyphenyl)amino-3-amino-pyridine, 2,3-diamino-6-methoxypyridine, 2-(β-methoxyethyl)amino-3-amino-6-methoxypyridine, 3,4-diaminopyridine, and the addition salts thereof with an acid.

Among the pyrimidine derivatives, exemplary mention may be made of the compounds described, for example, in German patent DE 2 359 399 or Japanese patents JP 88-169 571 and JP 91-10659 or International patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in patent application FR-A-2 750 048 and among which exemplary mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-imidazolylpropylaminopyrazolo[1,5-a]pyrimidine; and the addition salts thereof and tautomeric forms thereof, when a tautomeric equilibrium exists.

Among the pyrazole derivatives, exemplary mention may be made of the compounds described in patents DE 3 843 892 and DE 4 133 957 and patent applications WO 94/08969, WO 94/08970, FR-A-2 733 749 and DE 195 43 988, such as 4,5-diaminopyrazoles, for instance 4,5-diamino-1-methylpyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole; 3,4-diaminopyrazole; 4-amino-1,3-dimethyl-5-hydrazinopyrazole; 3,4,5-triaminopyrazoles, for instance 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole; and the addition salts thereof with an acid.

In at least one embodiment, a 4,5-diaminopyrazole is used, such as 4,5-diamino-1-(β-hydroxyethyl)pyrazole or a salt thereof.

As pyrazole derivatives, exemplary mention may also be made of diamino-N,N-dihydropyrazolopyrazolones, for instance those described in application FR-A-2 886 136, such as the following compounds and addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

In at least one embodiment, 2,3-diamino-6,7-dihydro-1H, 5H-pyrazolo[1,2-a]pyrazol-1-one and/or an addition salt thereof will be used.

In some embodiments, as heterocyclic bases, 4,5-diamino-1-(β-hydroxyethyl)pyrazole and/or 2,3-diamino-6,7-dihydro-1H,5H-pyrazolo[1,2-a]pyrazol-1-one and/or an addition salt thereof will be used.

As cationic oxidation bases that can be used in the compositions according to the disclosure, mention may, for example, be made of the following compounds: para-phenylenediamines, for example those described in patent applications FR-A-2 766 177 and FR-A-2 766 178, para-aminophenols as described, for example, in patent applications FR-A-2 766 177 and FR-A-2 766 178, ortho-phenylenediamines as described, for example, in patent applications FR-A-2 782 718, FR-A-2 782 716 and FR-A-2 782 719, ortho-aminophenols or double bases which are cationic, such as derivatives of bis(aminophenyl)alkylenediamine type, described in patent application FR-A-2 766 179, and also cationic heterocyclic bases, these compounds bearing at least one quaternary nitrogen atom.

In at least one embodiment, the at least one cationic oxidation base that can be used in the compositions according to the disclosure is chosen from cationic para-phenylenediamines.

In some embodiments, the at least one cationic oxidation base is chosen from cationic oxidation bases of para-phenylenediamine structure, at least one of the amine functions of which is a tertiary amine bearing a pyrrolidine ring, the molecule having at least one quaternized nitrogen atom. Such bases are, for example, described in document EP-A-1 348 695.

The at least one oxidation base can be present in the composition in a total amount ranging from 0.0005% to 12% by weight relative to the total weight of the composition. For example, the at least one oxidation base is present in a total amount ranging from 0.005% to 8% by weight, or for example from 0.05% to 5% by weight relative to the total weight of the composition.

For example, the at least one coupler that can be used in the composition according to the disclosure can be chosen from those conventionally used in oxidation dyeing compositions, i.e. meta-aminophenols, metaphenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

In at least one embodiment, the at least one coupler is chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo-[3,2-c]-1,2,4-triazole, 2,6-dimethylpyrazolo-[1,5-b]-1,2,4-triazole, and the addition salts thereof with an acid.

According to at least one embodiment, the composition of the disclosure comprises at least one coupler bearing at least one amino group, which is optionally substituted, and for instance may be chosen from aminophenols and meta-phenylenediamine couplers. According to one embodiment, the composition comprises at least one NH2 group.

For example, the composition according to the disclosure may comprise at least one coupler in a total amount ranging from 0.0001% to 15% by weight relative to the total weight of the composition. In at least one embodiment, the at least one coupler is present in a total amount ranging from 0.001% to 10% by weight relative to the total weight of the composition, such as from 0.01% to 8% by weight relative to the total weight of the composition.

In at least one embodiment, the at least one oxidation bases and/or at least one coupler may be present in the composition of the disclosure in the form of addition salts, for example in the form of addition salts with an acid.

In some embodiments, the addition salts with an acid that can be used in the context of the disclosure are chosen from hydrochlorides, hydrobromides, sulfates, citrates, succinates, tartrates, lactates, acetates, alkyl sulfates and alkyl sulfonates.

For example, when the at least one oxidation bases or at least one couplers contains at least one carboxylic acid or sulfonic acid function, addition salts with a base can be envisioned. The addition salts with a base that can be used in a context of the dye compositions of the disclosure are then, for example, those obtained with sodium hydroxide, potassium hydroxide, aqueous ammonia or amines.

According to at least one embodiment of the disclosure, the composition comprises at least one additional oxidation base other than N,N-bis(β-hydroxyethyl)-para-phenylenediamines and the addition salts thereof with an acid, and at least one coupler.

According to at least one embodiment, the at least one additional oxidation base is chosen from para-aminophenols, heterocyclic bases and the addition salts thereof with an acid.

The composition in accordance with the present disclosure comprises at least one oxidizing agent.

The at least one oxidizing agent is chosen, for example, from peroxides such as hydrogen peroxide and urea peroxide, bromates and ferricyanides of alkali metals, and persalts such as perborates, percarbonates and persulfates. For example, the at least one oxidizing agent may also be at least one oxidoreduction enzyme such as laccases, peroxidases and 2-electron oxidoreductases (such as uricase), optionally in the presence of their respective donor or cofactor.

In at least one embodiment, the at least one oxidizing agent comprises hydrogen peroxide. In some embodiments, this oxidizing agent may, for example, comprise aqueous hydrogen peroxide, the titer of which ranges, for example, from 1 to 40 volumes, for example from 5 to 40 volumes.

In at least one embodiment, the at least one oxidizing agent is present in the composition of the disclosure in a total amount ranging from 0.1% to 20% relative to the total weight of the composition, such as from 0.5% to 10% relative to the total weight of the composition.

The composition of the disclosure may optionally comprise at least one alkaline agent. The at least one alkaline agent is, for example, chosen from aqueous ammonia, alkali metal carbonates or bicarbonates, for instance sodium carbonate or bicarbonate or potassium carbonate or bicarbonate, alkanolamines such as mono-, di- and triethanolamines, and derivatives thereof, hydroxyalkylamines and ethylenediamines which are oxyethylenated and/or oxypropylenated, sodium hydroxide, potassium hydroxide, amino acids, and basic amino acids such as arginine or lysine, and the compounds of formula (V):

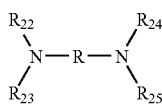 (V)

wherein:
R is a propylene residue optionally substituted with a hydroxyl group or a $C_1$-$C_4$ alkyl radical;
$R_{22}$, $R_{23}$, $R_{24}$ and $R_{25}$, which may be identical or different, represent a hydrogen atom, a $C_1$-$C_4$ alkyl radical or a $C_1$-$C_4$ hydroxyalkyl radical.

According to at least one embodiment, the composition comprises a small amount of aqueous ammonia, or, in at least one embodiment, no aqueous ammonia. According to this embodiment, the composition comprises at least one alkanolamine, such as monoethanolamine or 2-amino-2-methyl-1-propanol.

According to at least one embodiment, the composition comprises as alkaline agent at least one organic amine, for example, at least one alkanolamine. When the composition comprises more than one alkaline agent chosen from alkanolamine, ammonium hydroxides, and salts thereof, the at least one organic amine is present in a total amount that is greater than the total amount of ammoniac.

The at least one alkaline agent can be present in the composition of the disclosure in an amount ranging from 0.01% to 30% by weight relative to the total weight of the composition, for example from 0.1% to 20% relative to the total weight of the composition.

For example, the dye composition in accordance with the disclosure may also comprise at least one direct dye that, in at least one embodiment, may be chosen from nitrobenzene dyes, azo direct dyes, methine direct dyes, and the addition salts thereof. These direct dyes may be of nonionic, anionic or cationic nature.

For example, the composition may also contain other compounds constituting the dyeing medium. For example, this dyeing medium may comprise water or a mixture of water and at least one cosmetically acceptable organic solvent, which, in at least one embodiment is water-soluble.

As examples of organic solvents, mention may be made of alcohols such as ethyl alcohol, isopropyl alcohol, benzyl alcohol and phenylethyl alcohol, or glycols or glycol ethers such as, for example, monomethyl, monoethyl or monobutyl ethers of ethylene glycol, propylene glycol or its ethers, such as, for example, propylene glycol monomethyl ether, butylene glycol, hexylene glycol, dipropylene glycol and also diethylene glycol alkyl ethers such as, for example, diethylene glycol monoethyl ether or diethylene glycol monobutyl ether. For example, the at least one solvent, when present, may be present in a total amount ranging from 0.01% to 35% by weight relative to the total weight of the composition, for example from 0.1% to 25% by weight, relative to the total weight of the composition.

In at least one embodiment, the composition of the disclosure comprises water. In some embodiments, the water is present in an amount ranging from 10% to 70% relative to the total weight of the composition, for example from 20% to 55% relative to the total weight of the composition.

The composition in accordance with the disclosure may also contain at least one adjuvant conventionally used in hair-dyeing compositions.

The term "adjuvant" is intended to mean an additive other than the abovementioned compounds.

As examples of adjuvants that can be used, mention may be made of anionic, cationic, nonionic, amphoteric or zwitterionic surfactants, or mixtures thereof; anionic, cationic, nonionic, amphoteric or zwitterionic polymers, inorganic or organic thickeners, such as anionic, cationic, nonionic and amphoteric associative polymeric thickeners, other than the associative celluloses according to the disclosure; antioxidants or reducing agents; penetrating agents; sequestering agents; fragrances; buffers; dispersing agents; conditioning agents such as, for example, volatile or nonvolatile silicones, which may be modified or unmodified; film-forming agents; ceramides, preservatives; opacifiers; and antistatic agents.

In at least one embodiment, the composition of the disclosure comprises at least one surfactant.

In some embodiments, the at least one surfactant is chosen from nonionic surfactants and anionic surfactants.

In at least one embodiment, the at least one anionic surfactant is chosen from the salts (such as alkali metal salts, for instance sodium salts, ammonium salts, amine salts such as amino alcohol salts, or alkaline-earth metal salts, for instance magnesium salt) of:
alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefin sulfonates, paraffin sulfonates;
alkyl phosphates, alkyl ether phosphates;
alkylsulfosuccinates, alkyl ether sulfosuccinates, alkylamidesulfosuccinates, alkylsulfosuccinamates;
alkylsulfoacetates;
acylsarcosinates; acyl isethionates and N-acyltaurates;
salts of fatty acids such as oleic acid, ricinoleic acid, palmitic acid or stearic acid, coconut oil acid or hydrogenated coconut oil acid;
alkyl-D-galactoside uronic acid salts;
acyllactylates; and
salts of polyoxyalkylenated alkyl ether carboxylic acids, of polyoxyalkylenated alkylaryl ether carboxylic acids or of polyoxyalkylenated alkylamido ether carboxylic acids, for example those containing from 2 to 50 ethylene oxide groups;
and mixtures thereof.

It should be noted that the alkyl or acyl radical of these various compounds may, for example, contain from 6 to 24 carbon atoms, for instance from 8 to 24 carbon atoms, the aryl radical in at least one embodiment denoting a phenyl or benzyl group.

In some embodiments, the at least one nonionic surfactant is chosen from monooxyalkylenated and polyoxyalkylenated, monoglycerolated and polyglycerolated nonionic surfactants. In at least one embodiment, the oxyalkylene units are chosen from oxyethylene and oxypropylene units, and combinations thereof, such as oxyethylene units.

As examples of oxyalkylenated nonionic surfactants, mention may be made of:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_8$-$C_{30}$ amides,
esters of saturated or unsaturated, linear or branched $C_3$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils,
condensates of ethylene oxide and/or of propylene oxide, inter alia, alone or as mixtures.

In at least one embodiment, the at least one surfactant comprises ethylene oxide and/or propylene oxide in an amount ranging from 1 mol to 50 mol, for example from 2 mol to 30 mol. In at least one embodiment, the at least one nonionic surfactant does not comprise any oxypropylenated units.

In accordance with at least one embodiment of the disclosure, the at least one oxyalkylenated nonionic surfactant is chosen from oxyethylenated $C_8$-$C_{30}$ and oxyethylenated $C_{18}$-$C_{30}$ alcohols.

As examples of monoglycerolated or polyglycerolated nonionic surfactants, monoglycerolated or polyglycerolated $C_8$-$C_{40}$ alcohols may be used.

In some embodiments, the monoglycerolated or polyglycerolated $C_8$-$C_{40}$ alcohols correspond to the formula below:

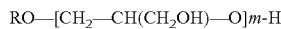

RO—[$CH_2$—CH($CH_2$OH)—O]$m$-H wherein R represents a linear or branched $C_8$-$C_{40}$, such as $C_8$-$C_{30}$, alkyl or alkenyl radical, and m represents a number ranging from 1 to 30, such as from 1 to 10.

As examples of compounds that are suitable in the context of the disclosure, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

In at least one embodiment, the monoglycerolated or polyglycerolated alcohols are chosen from $C_8$/$C_{10}$ alcohols containing 1 mol of glycerol, $C_{10}$/$C_{12}$ alcohols containing 1 mol of glycerol and $C_{12}$ alcohols containing 1.5 mol of glycerol.

In at least one embodiment, the at least one surfactant present in the composition of the disclosure is a nonionic surfactant.

For example, the at least one surfactant may be present in the composition of the disclosure in an amount ranging from 0.1% to 50% by weight relative to the total weight of the composition, such as from 0.5% to 30% by weight, relative to the weight of the composition.

The above adjuvants may, for example, be present in an amount, for each of them, ranging from 0.01% to 20% by weight, relative to the total weight of the dye composition.

Of course, those skilled in the art will take care to select the optional adjuvant(s) mentioned above in such a way that the effective properties intrinsically associated with the compositions of the disclosure are not, or are not substantially, impaired by the addition (or additions) envisioned.

The pH of the composition in accordance with the disclosure may range from 3 to 12, such as from 5 to 11, or such as from 7 to 11. It may be adjusted to the desired value via acidifying or basifying agents that are normally used in the dyeing of keratin fibers, or alternatively by means of conventional buffer systems.

The alkaline agents include, for example, those previously described.

Among the acidifying agents, mention may be made, as examples, of inorganic or organic acids such as hydrochloric acid, ortho-phosphoric acid, carboxylic acids such as tartaric acid, citric acid or lactic acid, or sulfonic acids.

The dye composition according to the disclosure may be in various forms, such as in the form of liquids, creams or gels, or in any other form suitable for dyeing keratin fibers, such as human hair.

The process of the present disclosure is a process in which the composition according to the present disclosure as defined above is applied to fibers. The color may be revealed at acidic, neutral or alkaline pH and the at least one oxidizing agent may be added just at the time of use or it may be used simultaneously with or sequentially to the other compounds of the composition of the disclosure. In at least one embodiment, this coloring is revealed at neutral pH.

After a leave-in time, for example ranging from 1 to 60 minutes, such as from 5 to 45 minutes, the keratin fibers may be rinsed, optionally washed with shampoo and rinsed again, and then dried.

In at least one embodiment, the composition according to the disclosure may result from the mixing of at least two compositions, such as two or three compositions, for example including an oxidizing composition comprising at least one oxidizing agent as defined above.

Another aspect of the disclosure is a multicompartment dyeing device or dyeing "kit" wherein at least one compartment contains a first composition comprising at least one fatty substance, at least one compartment contains a second composition comprising at least one oxidation base chosen from N,N-bis(β-hydroxyethyl)-para-phenylenediamines and the addition salts thereof with an acid; at least one dye precursor different than the at least one oxidation base; and at least one alkaline agent; and at least one compartment contains a third composition comprising at least one oxidizing agent; wherein the at least one third composition optionally comprises at least one fatty substance. In this embodiment, the composition comprising the at least one fatty substance may, for example, be anhydrous. As used herein, the term "anhydrous composition" is intended to mean a cosmetic composition which has a water content of less than 5% by weight relative the total weight of the composition, such as less than 2% by weight, or such as less than 1% by weight, relative to the total weight of the composition. It should be noted that this water may, for example, be bound water, such as the water from the crystallization of the salts or traces of water absorbed by the starting materials used in the preparation of the compositions according to the disclosure.

According to at least one embodiment, the device or kit of the disclosure comprises at least one compartment containing a first composition comprising at least one fatty substance and at least one oxidizing agent; and at least one compartment containing a second composition comprising at least one oxidation base chosen from N,N-bis(β-hydroxyethyl)-para-phenylenediamines and the addition salts thereof with an acid, at least one dye precursor different than the at least one oxidation base, and at least one alkaline agent. This device may, for example, be fitted with an applicator for delivering the desired mixture onto the hair, such as the devices described in patent FR-A-2 586 913 in the name of the applicant.

According to another embodiment, the device or kit of the disclosure comprises: at least one compartment containing a first composition comprising at least one fatty substance, at least one oxidation base chosen from N,N-bis(β-hydroxyethyl)-para-phenylenediamines and the addition salts thereof with an acid, at least one dye different than the at least one oxidation base, and at least one alkaline agent; and at least one compartment containing a second composition comprising at least one oxidizing agent.

Another aspect of the present disclosure is the use of a dye composition as defined above, for the oxidation dyeing of keratin fibers, such as human keratin fibers such as the hair.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below. The examples which follow are intended to illustrate the disclosure without, however, limiting the scope thereof.

In these examples, all the amounts are indicated as percent by weight of active material (A.M.) relative to the total weight of the composition, unless otherwise indicated.

EXAMPLE

The following compositions were prepared:

| Composition 1 | Concentration (g %) |
|---|---|
| DISTEARDIMONIUM HECTORITE | 3 |
| OCTYLDODECANOL | 11.5 |
| GLYCOL DISTEARATE | 8 |
| LIQUID PETROLEUM JELLY | 64.5 |
| PROPYLENE CARBONATE | 1 |
| LAURETH-2 | 1 |
| POLYSORBATE 21 | 11 |

| Composition 2 | Concentration (g %) |
|---|---|
| SEQUESTERING AGENT | 1 |
| SODIUM METABISULFITE | 0.7 |
| MONOETHANOLAMINE | 14.5 |
| 1-METHYL-2,5-DIAMINOBENZENE | 7.25 |
| N,N-BIS(2-HYDROXYETHYL)-P-PHENYLENEDIAMINE SULFATE. 1H$_2$O | 0.58 |
| 1,3-DIHYDROXYBENZENE | 5.8 |
| 1-HYDROXY-3-AMINOBENZENE | 1.45 |
| 1-BETA-HYDROXYETHYLOXY-2,4-DIAMINOBENZENE DIHYDROCHLORIDE | 0.58 |
| NATROSOL 250 HHR (hydroxyethylcellulose) | 1.5 |
| HEXYLENE GLYCOL | 3 |
| DIPROPYLENE GLYCOL | 3 |
| ETHYL ALCOHOL | 8.25 |
| PROPYLENE GLYCOL | 6.2 |
| ASCORBIC ACID | 0.25 |
| WATER | Qs 100 g |

| Composition 3 | Concentration (g %) |
|---|---|
| PENTASODIUM PENTETATE | 0.15 |
| HYDROGEN PEROXIDE IN SOLUTION AT 50% (200 VOL. AQUEOUS HYDROGEN PEROXIDE) | 12 |
| SODIUM STANNATE | 0.04 |
| TETRASODIUM PYROPHOSPHATE | 0.03 |
| LIQUID PETROLEUM JELLY | 20 |
| HEXADIMETHRINE CHLORIDE (AM at 60% in water) | 0.25 |
| POLYQUATERNIUM-6 (AM at 40% in water) | 0.5 |
| WATER | 54.1 |
| GLYCEROL | 0.5 |
| CETYLSTEARYL ALCOHOL (C16/C18 30/70) OXYETHYLENATED (33 EO) | 8 |
| CETYLSTEARYL ALCOHOL PROTECTED OXYETHYLENATED (4 EO) | 3 |
| RAPESEED ACID AMIDE at 92.3% in water | 1.3 |
| VITAMIN E | 0.1 |
| PHOSPHORIC ACID | Qs pH 2.2 |

The three compositions were mixed at the time of use, in the following proportions: 10 g of composition 1 with 4 g of composition 2 and 16 g of composition 3. The mixture was applied to locks of natural grey hair containing 90% of white hairs, in a proportion of 10 g of mixture per 1 g of hair. After a leave-in time of 30 min, the hair was rinsed, washed with a standard shampoo and dried.

The hair coloring was evaluated visually.

| Example 1 | Intense black |
|---|---|

Example 2

The following compositions were prepared (quantity expressed in g)

| | A3 (Comparative Composition) | A4 (Inventive Composition) |
|---|---|---|
| Isopropyle Myristate | 52 | 87 |
| Oleth-10 | 10 | 10 |
| Disteardimonium hectorite | 2.25 | 2.25 |
| Propylene Carbonate | 0.75 | 0.75 |
| Water | 35 | — |

Composition B' (in grams)

| | |
|---|---|
| N,N-bis(2-hydroxyethyl) p-phenylenediamine sulfate hydrate | 4.524 |
| 6-hydroxy benzomorpholine | 2.1895 |
| Hydroxyethyl cellulose (NATROSOL 250 HHR) | 1.5 |
| Dipropylene glycol | 3 |
| Hexylene glycol | 3 |
| Propylene glycol | 6.2 |

-continued

| Monoethanolamine | 15.92 |
|---|---|
| Ethanol | 8.25 |
| Reducing agents, sequestering agents, | qs |
| water | Qs 100 |

Composition C (in grams)

| Hydrogen peroxide | 6 |
|---|---|
| Cetearylic Alcohol | 2.28 |
| Ceteareth-25 | 0.57 |
| Trideceth-2 carboxamide MEA | 0.85 |
| Glycerine | 0.5 |
| Stabilizing agents, sequestering agents | Qs |
| Phosphoric Acid | Qs pH = 2 |
| water | Qs 100 |

The compositions A3 and A4 were each mixed together with the compositions B and C at the time of use in the following proportions: 10 g of composition A3 or A4 with 4 g of composition B' and 15 g of composition C.

The resulting mixtures were then applied on natural hair with 90% of white hair and on permed hair with 90% of white hair at the rate of 14.5 g of mixture for 1 g of hair. After a leave-on time of 30 minutes, the hair was rinsed, washed with a standard shampoo and dried.

The colour of the hair was determined by using the Datacolor SF600X spectraflash (illuminant D65, angle 10°, specular components included) in the L*a*b* system.

According to this system, L* indicates the lightness. The lowest is the value of L*, the most intense is the color of the hair. The chromaticity coordinates are expressed by the parameters a* and b*, a* indicating the axis of red/green shades and b the axis of yellow/blue shades.

Selectivity:

The selectivity of the color on hair was also evaluated.

The selectivity of the coloration is the variation of the color between natural colored hair and the highly sensitized colored hair. The selectivity ΔE is calculated from the following formula:

$$\Delta E = \sqrt{(L^* - L_o^*)^2 + (a^* - a_o^*)^2 + (b^* - b_o^*)^2}$$

wherein L* indicates lightness and a* and b* are the chromaticity coordinates of the permed colored locks whereas L0* indicates the lightness and $a_0^*$ and $b_0^*$ are the chromaticity of the natural colored locks. The lower the value of ΔE, the weaker selectivity the coloration and the more uniform the color of the hair along the fiber from the roots to the hair.

| Mixture | Hair Type | L* | a* | b* | ΔE |
|---|---|---|---|---|---|
| A3 + B' + C | BN | 29.7 | −0.6 | 4.8 | 11.1 |
|  | BP | 19.2 | −0.4 | 1.3 |  |
| A4 + B' + C (inventive) | BN | 28.9 | −0.6 | 3.8 | 7.7 |
|  | BP | 21.4 | −0.6 | 2.3 |  |

The mixture obtained with the composition A4 provided a color with a weaker selectivity, thus a better homogeneity of the color, than the one obtained from the mixture obtained with the composition A3.

What is claimed is:

1. A composition for the oxidation dyeing of keratin fibers, comprising:
    at least one fatty substance present in an amount greater than or equal to 25% by weight relative to the total weight of the composition,
    at least one oxidation base chosen from N,N-(β-hydroxyethyl)-para-phenylenediamines and the addition salts thereof with an acid,
    at least one dye precursor different than the at least one oxidation base chosen from N,N-(β-hydroxyethyl)-para-phenylenediamines and the addition salts thereof with an acid,
    at least one oxidizing agent, and
    optionally at least one alkaline agent.

2. The composition according to claim 1, wherein the at least one fatty substance is chosen from compounds which are liquid or pasty at ambient temperature and at atmospheric pressure.

3. The composition according to claim 1, wherein the at least one fatty substance is at least one fatty substance other than fatty acid.

4. The composition according to claim 1, wherein the at least one fatty substance is chosen from alkanes, fatty alcohols, fatty acid esters, fatty alcohol esters, oils and waxes.

5. The composition according to claim 1, wherein the at least one fatty substance is non-silicone-based.

6. The composition according to claim 1, wherein the at least one dye precursor different than the at least one oxidation base chosen from N,N-(β-hydroxyethyl)-para-phenylenediamines and the addition salts thereof with an acid is chosen from oxidation bases and couplers.

7. The composition according to claim 6, wherein the at least one dye precursor different than the at least one oxidation base chosen from N,N-(β-hydroxyethyl)-para-phenylenediamines and the addition salts thereof with an acid, is chosen from ortho- and para-phenylenediamine oxidation bases, double bases, ortho- and para-aminophenols, heterocyclic bases and the addition salts thereof with an acid.

8. The composition according to claim 7, wherein the at least one dye precursor different than the at least one oxidation base chosen from N,N-(β-hydroxyethyl)-para-phenylenediamines and the addition salts thereof with an acid, is chosen from para-aminophenol oxidation bases, heterocyclic bases and the addition salts thereof with an acid.

9. The composition according to claim 4, wherein the at least one dye precursor different than the at least one oxidation base chosen from N,N-(β-hydroxyethyl)-para-phenylenediamines and the addition salts thereof with an acid, is chosen from meta-aminophenol couplers, meta-phenylenediamines, meta-diphenols, naphthols, heterocyclic couplers and the addition salts thereof with an acid.

10. The composition according to claim 1, wherein the at least one oxidizing agent is a peroxide.

11. The composition according to claim 1, wherein the at least one alkaline agent is chosen from ammonia and alkanolamine.

12. A process for dyeing keratin fibers, comprising
    applying to keratin fibers for a period of time sufficient to develop the desired coloring a composition comprising:
    at least one fatty substance present in an amount greater than or equal to 25% by weight relative to the total weight of the composition,
    at least one oxidation base chosen from N,N-(β-hydroxyethyl)-para-phenylenediamines and the addition salts thereof with an acid, at least one dye precursor different than the at least one oxidation base chosen from N,N-(β-hydroxyethyl)-para-phenylenediamines and the addition salts thereof with an acid, at least one oxidizing agent, and optionally at least one alkaline agent.

13. A multicompartment kit comprising:

at least one compartment containing a composition comprising at least one fatty substance, at least one compartment containing a composition comprising at least one oxidation base chosen from N,N-bis(β-hydroxyethyl)-para-phenylenediamines and the addition salts thereof with an acid, at least one dye precursor other than the at least one oxidation base chosen from N,N-(β-hydroxyethyl)-para-phenylenediamines and the addition salts thereof with an acid, and at least one alkaline agent, and at least one compartment containing a composition comprising at least one oxidizing agent, and optionally at least one fatty substance;

wherein, when the compositions of the kit are combined, the at least one fatty substance is present in a total amount greater than or equal to 25% by weight relative to the total weight of the combined composition.

14. A multicompartment kit comprising:

at least one compartment containing a composition comprising at least one fatty substance and at least one oxidizing agent, and at least one compartment containing a composition comprising at least one oxidation base chosen from N,N-bis(β-hydroxyethyl)-para-phenylenediamines and the addition salts thereof with an acid, at least one dye precursor different than the at least one oxidation base chosen from N,N-(β-hydroxyethyl)-para-phenylenediamines and the addition salts thereof with an acid, and at least one alkaline agent;

wherein, when the compositions of the kit are combined, the at least one fatty substance is present in a total amount greater than or equal to 25% by weight relative to the total weight of the combined composition.

15. A multicompartment kit comprising:

at least one compartment containing a composition comprising at least one fatty substance, at least one oxidation base chosen from N,N-bis(β-hydroxyethyl)-para-phenylenediamines and the addition salts thereof with an acid, at least one dye precursor different than the at least one oxidation base chosen from N,N-(β-hydroxyethyl)-para-phenylenediamines and the addition salts thereof with an acid, and at least one alkaline agent, and at least one compartment containing a composition comprising at least one oxidizing agent;

wherein, when the compositions of the kit are combined, the at least one fatty substance is present in a total amount greater than or equal to 25% by weight relative to the total weight of the combined composition.

16. The composition according to claim 9, wherein the at least one dye precursor different than the at least one oxidation base chosen from N,N-(β-hydroxyethyl)-para-phenylenediamines and the addition salts thereof with an acid is chosen from aminophenol couplers and meta-phenylenediamine couplers.

17. The composition according to claim 10, wherein the at least one oxidizing agent is hydrogen peroxide.

18. The composition according to claim 11, wherein the at least one alkaline agent is an alkanolamine.

* * * * *